US010471105B1

(12) United States Patent
Ali et al.

(10) Patent No.: US 10,471,105 B1
(45) Date of Patent: Nov. 12, 2019

(54) METHOD FOR TREATING INFERTILITY

(71) Applicants: Jassim M. Hassan M. Ali, Safat (KW); Waleed M. Renno, Safat (KW)

(72) Inventors: Jassim M. Hassan M. Ali, Safat (KW); Waleed M. Renno, Safat (KW)

(*) Notice: Subject to any disclaimer, the term of this patent is extended or adjusted under 35 U.S.C. 154(b) by 0 days.

(21) Appl. No.: 16/527,992

(22) Filed: Jul. 31, 2019

Related U.S. Application Data

(60) Provisional application No. 62/813,799, filed on Mar. 5, 2019.

(51) Int. Cl.
*A61K 35/60* (2006.01)
*A61K 9/00* (2006.01)
*A61K 9/20* (2006.01)

(52) U.S. Cl.
CPC ............ *A61K 35/60* (2013.01); *A61K 9/0019* (2013.01); *A61K 9/0053* (2013.01); *A61K 9/20* (2013.01); *A61K 2236/333* (2013.01); *A61K 2236/39* (2013.01)

(58) Field of Classification Search
CPC .................................................. A61K 35/60
See application file for complete search history.

(56) References Cited

U.S. PATENT DOCUMENTS

| | | |
|---|---|---|
| 5,658,594 A | 8/1997 | Al-Hassan |
| 5,912,018 A | 6/1999 | Al-Hassan |
| 8,551,532 B2 | 10/2013 | Al-Hassan |
| 10,406,205 B1* | 9/2019 | Ali ............................ A61P 3/10 |
| 2013/0108705 A1* | 5/2013 | Al-Hassan ............ A61K 35/60 |
| | | 424/537 |

OTHER PUBLICATIONS

Al-Hassan et al., "Skin Preparations from Catfish (*Arius bilineatus*, Val.) Contain a Lipid Which Inhibits Cancer Cell Survival In Vitro," The FASEB Journal, vol. 30, No. 1 supplement, Apr. 1, 2016.
Yang et al., "Abstract 2246: Anti-proliferative activities of lipid fraction of extract from the skin of the catfish *Arius bilineatus*, Valenciennes," AACR Annual Meeting 2017; Apr. 1-5, 2017; Washington, DC.

* cited by examiner

*Primary Examiner* — Rosanne Kosson
(74) *Attorney, Agent, or Firm* — Richard C. Litman; Nath, Goldberg & Meyer

(57) ABSTRACT

A method of treating infertility in males can include administering a therapeutically effective amount of a composition comprising a soluble protein fraction obtained by fractionating epidermal gel secretions of catfish to a patient in need thereof. The soluble protein fraction can include soluble proteins and lipids obtained by fractionating the epidermal gel secretions of catfish. The soluble protein fraction can include 87% soluble proteins and 13% lipids. The composition can be administered by intraperitoneal (IP) or subcutaneous (SC) injection or sublingual (SL). A method of preparing the soluble protein fraction can include collecting the epidermal gel secretion of catfish and preparing a soluble protein fraction having 87% soluble proteins and 13% lipids by weight.

20 Claims, 9 Drawing Sheets

METHOD FOR TREATING INFERTILITY

CROSS-REFERENCE TO RELATED APPLICATION

This application claims the benefit of U.S. Provisional Patent Application Ser. No. 62/813,799, filed Mar. 5, 2019.

BACKGROUND

1. Field

The disclosure of the present patent application relates to the use of a preparation from the epidermal gel secretions (EGS) of catfish for therapeutic purposes, and particularly, to a method for treating infertility in males, using a preparation from the epidermal gel secretions of catfish.

2. Description of the Related Art

Male infertility refers to a male's inability to cause pregnancy in a fertile female. Infertility is a common complication in diabetic men. Diabetes can have negative effects on the male reproductive system. For example, diabetes can lead to changes in hormonal and testicular structure. Diabetes can cause the loss of germ cells by apoptotic cell death. Prolonged hyperglycemia may also lead to the over production of ROS, which results in the disruption of spermatogenesis and induction of the apoptotic pathway leading to severe damage of the seminiferous epithelial cell layers. Conventional treatment options for male infertility are rarely effective.

The Arabian Gulf catfish (*Arius bilineatus* (Valenciennes) naturally exudes a proteinaceous gel-like material ("epidermal gel secretion") from its epidermis upon stress or injury. The epidermal gel secretion includes a complex mixture of biochemically and pharmacologically active components. Often times, however, the Arabian Gulf catfish (*Arius bilineatus* (Valenciennes) produces venoms from its venomous spines and venom glands near its pectoral spines which mix with secretions on the catfish skin. Additionally, since the gelatinous secretion is exuded while the catfish is still alive, contaminants other than the venom (such as feces, vomit and blood) are also often mixed with the epidermal secretion. It is critical that these contaminants are removed by thorough washing of the fish while the fish is still alive before the EGS is collected.

Thus, a method for treating infertility solving the aforementioned problems is desired.

SUMMARY

A method of treating infertility in males can include administering a therapeutically effective amount of a composition comprising a soluble protein fraction obtained by fractionating epidermal gel secretions of catfish to a patient in need thereof. The soluble protein fraction can include soluble proteins and lipids obtained by fractionating the epidermal gel secretions of catfish. The soluble protein fraction can include 87% soluble proteins and 13% lipids. The composition can be administered by intraperitoneal (IP) or sub-cutaneous (SC) injection or by sublingual (SL) administration. A method of preparing the soluble protein fraction can include collecting the epidermal gel secretion of catfish and fractionating the epidermal gel secretion of catfish after thorough washing of any contaminants on EGS caused by venom, blood, vomit, and feces, and after fractionating the epidermal gel secretion to obtain the soluble protein fraction.

Fractionating the epidermal gel secretion (EGS) of catfish can include mixing the catfish epidermal gel secretions with phosphate buffered saline to provide a solution containing EGS, homogenizing the solution with its contents of EGS to provide a homogenized extract, and centrifuging the homogenized extract to provide a soluble protein fraction and an insoluble protein fraction containing any cells or skin debris resulting from the EGS collection procedure. The soluble fraction can be freeze dried to provide a powdered soluble fraction and kept under nitrogen at $-80°$ C. If desired, the insoluble protein fraction can be fractionated (in the manner described above for fractionating the EGS) to collect any soluble proteins still left in the insoluble protein fraction to separate any undissolved soluble proteins therefrom. The additional soluble protein fraction extracted from the insoluble protein fraction can be added to the original soluble protein fraction to enrich the original soluble protein fraction, freeze-dried and kept at $-80°$ C. in the dark under nitrogen until use.

The freeze-dried soluble fraction can be analyzed to determine a ratio of the concentration of soluble protein to lipids. It is critical that the freeze-dried powdered soluble fraction includes 87% soluble proteins and 13% lipids. If the freeze-dried powdered soluble fraction includes less than 13% lipids, however, the soluble fraction can be supplemented with lipids from an additional lipid fraction to provide a soluble protein fraction having 87% soluble proteins and 13% lipids. The additional lipid fraction can be obtained from a lipid extraction of a separate (another) preparation of the freeze-dried EGS. The therapeutic composition can include the freeze-dried soluble protein fraction having 87% soluble proteins and 13% lipids kept at about $-80°$ C. under nitrogen until use.

For administration of the composition, the soluble protein fraction can be taken out of deep freeze ($-80°$ C.), dissolved in saline in phosphate buffer (pH 7.5), and maintained at temperatures ranging from about $4°$ C. to about $6°$ C. The concentration of proteins in the composition can be evaluated after dissolution in buffered-saline and before the composition is administered. The protein concentration will determine how many mLs of the soluble composition should be administered to provide a total of 3 mg of soluble proteins per Kg body weight per day for the human or animal to be treated. Thus, the preparation to be administered is dissolved in buffered saline, and the soluble protein contents in a given volume of the solution are evaluated to provide 3 mg of soluble protein per kilogram of body weight in a given number of mLs (cc) before administration. This calibrated solution is divided into daily portions to be served daily to a patient, and kept at $-80°$ C. under nitrogen to be ready for use. By pre-preparing measured portions (volumes) of the composition that include 3 mg proteins per Kg body weight, daily dosages of the composition are ready for administration once per day to a patient according to the patient's weight. These measured preparations can be prepared separately for each patient according to the patient's weight before receiving the treatment. In an embodiment, the composition includes the soluble protein fraction dissolved in phosphate buffered saline. It is important to use the dissolved soluble protein fraction and administer the composition when the composition is still cold, e.g., temperatures ranging from about $4°$ C. to about $6°$ C. For example, the composition can be taken out of the −80° C. storage temperatures and maintained in crushed ice or in a refrigerator prior to administration.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
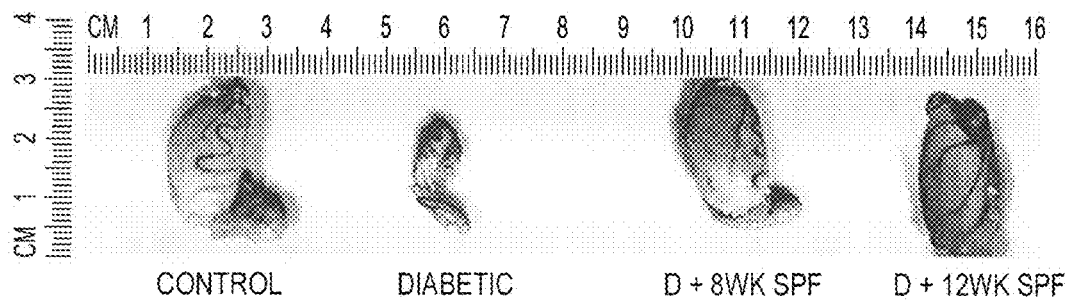
FIG. 1 is an image showing the respective sizes of testes collected from the experimental groups.
Figure 2A:
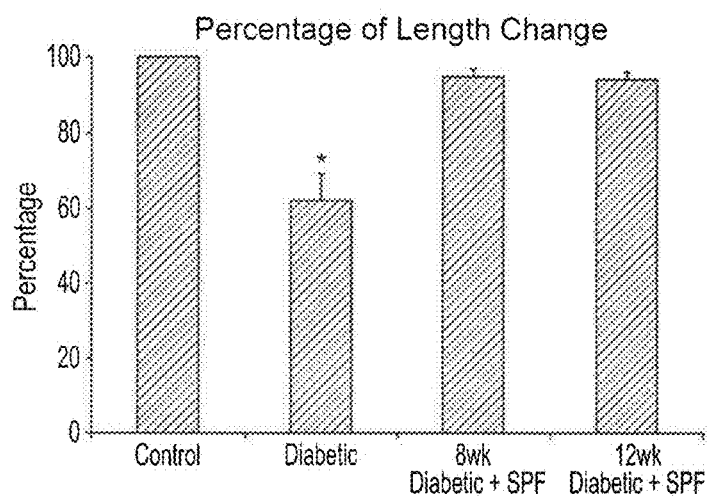
FIG. 2A is a graph showing the percentage of change in length of all of the experimental groups.
Figure 2B:
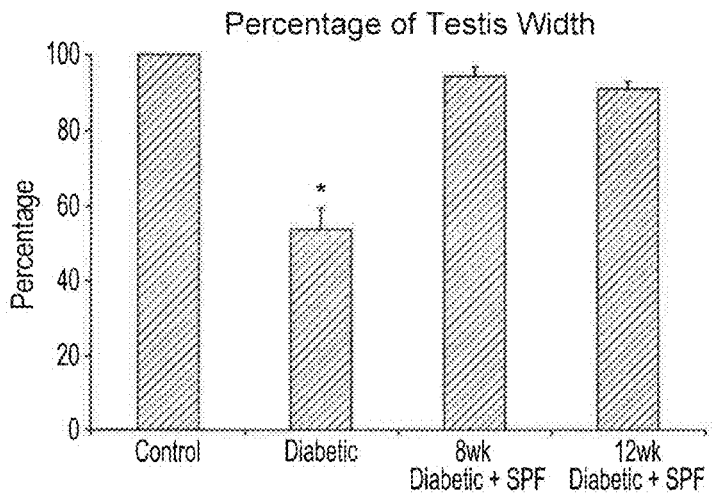
FIG. 2B is a graph showing the percentage of change in width of all of the experimental groups.
Figure 2C:
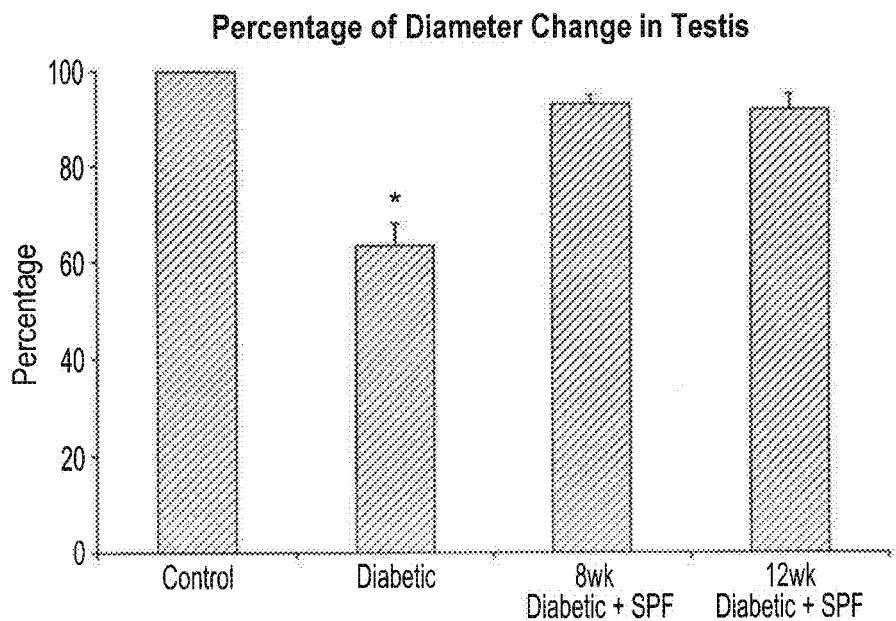
FIG. 2C is a graph showing the percentage of change in diameter of all of the experimental groups.
Figure 2D:
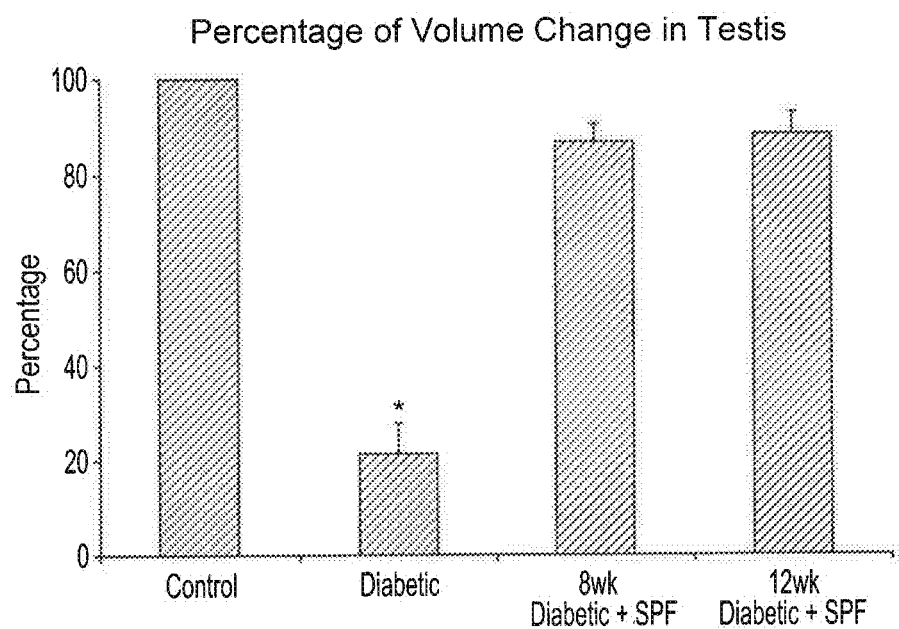
FIG. 2D is a graph showing the percentage of change in volume of all of the experimental groups.

A method for treating infertility can include administering a therapeutically effective amount of a composition comprising a soluble protein fraction obtained from epidermal gel secretions of catfish to a patient in need thereof. The soluble protein fraction can include soluble proteins and lipids. The soluble protein fraction can include 87% soluble proteins and 13% lipids. The composition can be administered by intraperitoneal (IP) or sub-cutaneous (SC) injection or by sublingual administration (SL). A method of preparing the soluble protein fraction can include collecting the epidermal gel secretion of catfish and fractionating the epidermal gel secretion to obtain the soluble protein fraction.

A method of preparing a therapeutic composition from the epidermal gelatinous secretion of catfish can include washing the living fish thoroughly to remove contaminants such as venom, blood, vomit, and feces.

A method of preparing a therapeutic composition from the epidermal gelatinous secretion of catfish can include collecting epidermal gel secretions (EGS) from the catfish and fractionating the epidermal gel secretions to obtain a soluble protein fraction comprising 87% soluble proteins and 13% lipids. The therapeutic composition can include the soluble protein fraction comprising 87% soluble proteins and 13% lipids.

The soluble protein fractions described herein can be obtained from the epidermal gel secretions (EGS) of Arabian Gulf catfish, such as (*Arius bilineatus* (Valenciennes)). The Arabian Gulf catfish naturally exudes a gelatinous secretion through its skin after the catfish is shocked, e.g., threatened or injured. For example, once a catfish is caught, it will struggle as it is towed to the surface with the fishing hook still in its mouth (as the catfish is a bottom dweller). As the fish reaches the surface, it struggles to defend itself and to escape the reduction in water pressure. This will cause the fish to secrete the EGS along with one or more contaminants, such as venom from its venom glands and dorsal and pectoral spines, feces from its anal pore, vomit from its mouth and through its gills, and blood through its gills if the fishing hook catches the gill rays. Shocking the fish can also be accomplished by thermal shock, physical abrasions, or neural stimulation or simply by the action of towing it to the surface of the sea with the fishing hook in its mouth. The fish is washed thoroughly while it is still alive to remove contaminants. While the fish is still alive, the fish can be held through its gills to induce production of additional EGS. The EGS without any remaining contaminants on the skin can be collected by a gentle mechanical scraping or suction of the skin. Preferably, the EGS is immediately frozen, e.g., in dry ice, then cooled to −80° C. (deep freeze) or kept frozen in liquid nitrogen, to limit microbial growth and prevent biochemical decomposition.

The soluble protein fractions described herein can include a mixture of highly active biochemical and pharmacological components. These include, for example, a plasma clotting factor that has been found to be specific to blood clotting factor X1, a hemolytic factor, platelet activating factors (PAFs) at unusually high levels (more than 5,000 times the threshold level required for normal platelet activation), and a hemagglutination factor. The soluble fraction can also include vaso-active components, phosphatases, including an acid phosphatase, a general esterase and a tyrosine specific esterase, and proteins with collagenase-like activities that cleave collagen into fragments. The soluble fraction can include a factor that activates phospholipase A2, tyrosine and serine/threonine protein phosphorylase, proteolytic and antimicrobial activities, leukotrienes, interleukin 1 and growth factors that affect macrophages and pancreatic β-cells, along with four protein components that are capable of binding human fibronectin. The lipids in the soluble fraction can include neutral lipids, phospholipids, and glycolipids. For example, the neutral lipids can include eicosanoids, cholesterol, cholesterol derivatives, triglycerides, fatty acids and steroids.

It should be understood that a therapeutic composition can be prepared from epidermal gel secretions of other species of catfish or any other aquatic or terrestrial creature (e.g., moray eels, slugs, and worms) that produces epidermal gel secretions having biologically active components similar to those present in the soluble protein fractions described herein.

According to an embodiment, the method of preparing a therapeutic composition from the epidermal gelatinous secretion of catfish can include collecting an epidermal gel secretion (EGS) from the skin of Arabian Gulf catfish (*Arius bilineatus*, Valenciennes) that is free from venom, vomit, feces, blood, or other contaminants from the fish, and fractionating the EGS to provide a soluble protein fraction (SPF).

In an embodiment, the soluble protein fraction (SPF) can be extracted from the EGS by thawing the EGS that was frozen at −80° C. to a temperature ranging from about 4° C. to about 6° C. and mixing the thawed EGS with a suitable, non-toxic ionic extraction buffer (e.g., saline in phosphate buffer at pH 7.5) to provide an extract. This step and all subsequent purification procedures can be carried out at about 4° C. to about 6° C. in the dark, unless otherwise indicated. The extraction buffer should not denature or affect the proteins in the EGS in any way. Preferably, the extraction buffer includes phosphate buffered saline having 0.05M ($NaH_2PO_4Na_2HPO_4$) and 0.14M NaCl, pH 7.5. The thawed EGS can be mixed with an equal volume of the extraction buffer and homogenized, e.g., with an Ultra Truex (IKA) homogenizer. The homogenized extract can then be centrifuged at 15000 rpm to provide a soluble protein fraction (SPF) and an insoluble protein fraction. Centrifugation can separate insoluble filamentous proteins and cellular debris from a soluble fraction. Centrifugation can also remove contaminants such as microorganisms. The therapeutic composition is preferably free from insoluble components, as such components are not appropriate for intra-peritoneal or sub-cutaneous injection and will not be absorbed and distributed if injected into an animal or human in this manner. Insoluble components can also clog the injection needle during injection. In an embodiment, the homogenate is centrifuged at 15,000 rpm for about ten to about fifteen minutes to provide the soluble fraction and the insoluble fraction. The soluble fraction can be freeze-dried and maintained at about −80° C. under nitrogen in the dark.

In an embodiment, the soluble protein fraction is freeze-dried and maintained at about −80° C. under nitrogen in the dark. The freeze-dried soluble fraction can be analyzed to determine a ratio of the concentration of soluble protein to lipids. In an embodiment, the powdered soluble fraction includes 87% soluble proteins and 13% lipids. If the powdered soluble fraction includes less than 13% lipids, the powdered soluble fraction can be supplemented with lipids from an additional lipid fraction to achieve a soluble protein fraction having 87% soluble proteins and 13% lipids. The additional lipid fraction can be obtained from a separate preparation of the freeze-dried EGS and added to the prepared freeze-dried proteins in isopropanol to raise the final lipid concentration to 13%. The therapeutic composition can include the soluble protein fraction having 87% soluble proteins and 13% lipids. The soluble fraction (SPF) (also referred to herein as "Fraction B") can be freeze-dried and stored at about −80° C. under nitrogen in the dark.

According to an embodiment, an additional soluble protein fraction can be separated from the insoluble fraction obtained from centrifugation. According to an embodiment, an insoluble fraction obtained from centrifugation in one fractionating cycle can be further fractionated in a subsequent fractionating cycle to provide yet another soluble protein fraction. According to an embodiment, the method can include about two to about four fractionating cycles of insoluble protein fractions, thereby providing a plurality of additional soluble protein fractions. The plurality of additional soluble protein fractions can be pooled and added to the original SPF obtained from the original fractionation of the EGS. The soluble protein fraction (SPF) or "Fraction B" can include the pooled soluble protein fractions. Once a concentration of 13% lipids and 87% proteins is achieved, the SPF can be used for IP injection in an animal or human for treating infertility in males. The SPF (Fraction B) should include by dry weight 87% soluble proteins and 13% lipids prior to administration.

Generally after the fractionating cycles described above, the concentration of the proteins in the soluble protein fraction can be assumed to be 87%, while the lipid concentration in the soluble protein fraction will need to be determined and adjusted (generally increased) to achieve a concentration of 13% of the total aggregate of the lipids and proteins. The concentration of lipids in the soluble protein fraction can be determined, e.g., by extracting the lipids from a freeze-dried soluble protein fraction and weighing the extracted lipids. Additional lipids for adding to the soluble protein fraction can be extracted directly from a separate preparation of freeze-dried EGS. Only an amount of additional lipids required to increase the lipid percentage to 13% is added to the freeze-dried soluble protein fraction in isopropanol. The additional lipids can be extracted from the freeze-dried original EGS. As described in detail, below, lipid extraction can be carried out in the dark and the extracted lipids can be stored under nitrogen in the dark at −80° C. until added to the soluble protein fraction. The required weight of the lipids can be dissolved in isopropyl alcohol and added to the freeze-dried soluble protein fraction intended to be used for therapeutic administration to increase the lipid concentration to 13% of the total soluble protein-lipid fraction by weight. The organic solvent can be evaporated under vacuum at room temperature.

While the soluble protein concentration can be assumed to be 87%, the lipid concentration should be measured and adjusted until a lipid concentration of 13% is achieved. Generally, after the fractionation cycles described above, the total aggregate concentration of the proteins and lipids will be less than 100%, with the remainder being ionic salts of the buffered saline. Additional lipids can be provided by extracting lipids from another freeze-dried preparation of EGS with organic solvent mixture. The additional lipids can be obtained from the freeze-dried EGS by extracting the lipids with an organic solvent mixture including chloroform:methanol:isopropanol (2:1:0.250, v/v) for about 72 hours on a stirring plate. The extracted lipids can then be obtained by filtration, e.g., using a vacuum pump and a Buchner funnel. The lipid extracts can be concentrated to dryness on a rotary evaporator at about 25° C. in the dark and then collected using a vacuum pump in the dark. The additional lipids can be weighed to ensure that the precise amount of lipids that is needed to raise the lipid concentration to 13% has been obtained. The additional lipids (in the precise amount that is needed) can be dissolved in isopropyl alcohol, and added to the soluble freeze-dried protein fraction to increase the lipid fraction in the soluble protein fraction to 13% of the combined weight of the proteins and lipids. The organic solvent can be evaporated under vacuum at room temperature in the dark to provide a freeze-dried soluble protein fraction having 87% soluble proteins and 13% lipids by weight of the total combined soluble proteins and lipids. The freeze-dried soluble protein fraction including 87% soluble proteins and 13% lipids, or Fraction B, can be stored under nitrogen in the dark at about −80° C. until needed for injection or can be made into tablets for sublingual administration. The freeze-dried soluble fraction can be maintained at about −80° C. (deep freeze) under nitrogen in the dark for long-term storage to prevent any unwanted chemical reaction. The enzymes and the lipids in the freeze-dried fraction will be stable if kept at about −80° C. in the dark under nitrogen during storage for lengthy periods of time. Also the lipids in the soluble protein fraction will be protected from decomposition if kept the same way in deep freeze until required for use. An atmosphere of nitrogen will prevent aerial oxygenation of the lipids. The SPF containing 87% proteins and 13% lipids is weighed out and dissolved in the buffered saline to provide 3 mg proteins per kilogram body weight preparations appropriate for a single injection per day and is stored at −80° C. in the dark. Just before administration, the frozen preparation can be thawed, kept in ice, and administered as needed.

A therapeutically effective amount of the composition including the SPF (Fraction B) can be administered to a patient to treat infertility in males. The therapeutic composition can be combined with a pharmaceutically acceptable carrier. A therapeutically effective amount can include 3 mg to 4 mg or 3 mg to 3.5 mg of the SPF (e.g., SPF including 87% soluble protein and 13% total lipids) per kilogram of body weight of the patient (animal or human) to be treated. The therapeutic composition can be administered to a patient in need thereof, by intraperitoneal (IP) or sub-cutaneous (SC) injection after dissolution of the SPF in saline, phosphate buffered saline, or other delivery system, such as nanotechnology delivery systems or a tablet to be applied sublingually (SL). If in tablet form, the tablet can be coated with a suitable protective coating. Prior to injection of the soluble protein fraction, the freeze-dried soluble fraction can be dissolved in saline or phosphate buffered saline. If the fraction is already dissolved in any of these solvents as weighed, ready to use portions, the fraction can be kept in crushed ice until ready for administration.

The therapeutic composition can be administered by oral administration, provided that the composition is protected from the digestive effects of the elementary canal for oral administration, such as by encapsulation or nano-particle technology. In an embodiment, the therapeutic composition can be administered orally through nanotechnology derived carriers.

The therapeutic composition can prevent apoptosis of the cells and tissues in the testes and provides recovery of the testes through regeneration, leading to a healthy, functional testis with sperm count and motility approximately similar to a normal fertile testis.

As described in detail herein, the therapeutic composition, prepared according to the present teachings, was administered to male rats with streptozotocin (STZ)-induced type 1 diabetes mellitus. The therapeutic composition improved stereological parameters, sperm analysis factors, and structural alterations in the rats. In particular, a strong therapeutic effect was demonstrated on sperm count and motility in the STZ-diabetic rats. The therapeutic composition improved testicular morphology and functions through modulating the apoptotic pathway in the testes of the STZ-diabetic rats.

The following examples illustrate the present teachings.

Example 1

Preparation of SPF and Calculation of Soluble Protein in Solution

EGS was collected from the catfish skin and kept at −80° C. until use. Frozen EGS was thawed to 4° C., mixed with an equal volume of extraction buffer [phosphate buffered saline (PBS), 0.05 M containing ($NaH_2PO4/Na_2HPO_4$) and 0.14 M NaCl, pH 7.5], and homogenized with an Ultra Truex (IKA) homogenizer. This step and all subsequent purification procedures were carried out at 4° C. unless otherwise indicated. The homogenate was centrifuged at 15,000 rpm for 10-15 min. The supernatant was collected, and the pellet (insoluble protein etc.) was re-extracted with extraction buffer (2-4 times). Each time, the soluble fraction was separated by centrifugation as described above, and the two extracted fractions were pooled. The combined extracted fractions provided the soluble protein fraction (SPF)

To find the concentration of catfish soluble proteins in the SPF, the SPF was diluted with PBS (1:50). 0.1 ml of the diluted sample was mixed well with 5 ml of Coomassie Brilliant Blue solution and kept in tubes at room temperature for about 10 minutes. Absorbance was read at 595 nm for the sample, and its protein concentration was determined by comparing its absorbance against absorbance for a standard curve for different bovine serum albumin concentrations.

The required weight (3 mg protein per kg body weight) of the prepared SPF (with 87% soluble proteins and 13% lipids, quantified and made ready for injection as described above) was then dissolved in the extraction buffer to be made ready for injection.

Example 2

Administration of SPF to Experimental SD Rats

Sprague-Dawley (SD) male rats were used as model experimental animals to show the efficacy of SPF (Fraction-B). The experimental SD rats were divided randomly into the following groups: I) Control normal SD rats; II) Control diabetic SD rats for 8 weeks; III) Diabetic SD rats treated with the soluble protein fraction (SPF; Fraction B) for 8 weeks after the animals became diabetic one week after the injection of STZ; and IV) Diabetic SD rats treated with Fraction-B for 12 weeks after the animals became diabetic one week after the injection of STZ.

The diabetic rats were injected with Fraction-B at the rate of 0.300 mg/100 gm body weight once every 24 hrs. One group was injected for 8 weeks and another for 12 weeks. The animals in groups I, II, III, and IV were sacrificed under anaesthesia at the end of the period and their testes were collected immediately and examined for sperm count and sperm motility. Histological and biochemical studies were done on the collected testes.

As set forth in the Examples below, the results of these studies revealed positive therapeutic effect on testes of STZ-induced diabetic rats following the 8- and 12-weeks treatment with Fraction B.

Example 3

Gross Features of the Testes

The testes collected from all of the STZ-induced diabetic control, untreated animals showed a remarkable decrease in size and shape compared to control rats. Interestingly, following 8- and 12-weeks treatment with Fraction B, the diabetic animals showed amazing increase in the size of their testes, reaching a size similar to normal control animals. The SPF Fraction −B treated testes eventually displayed normal shapes and sizes.

The gross dimensions (length, width, diameter and volume) of all the testes from all the experimental groups were measured and compared. Exemplary measurements from an animal in each group is provided in FIG. 1. The morphometric analysis revealed a significant decrease in the percentage of length (P<0.000) (FIG. 2A) and width (P<0.000) (FIG. 2B) changes in the diabetic untreated animals. Likewise, the percentage of diameter (P<0.000) (FIG. 2C) and volume (P<0.000) (FIG. 2D) showed a significant reduction compared to control animals. However, SPF Fraction-B treatment of diabetic animals for 8- and 12-weeks showed a significant (P<0.000) increase in the length, width, diameter, and volume parameters, achieving dimensions similar to normal control groups (FIGS. 2A-2D).

Figure 3:
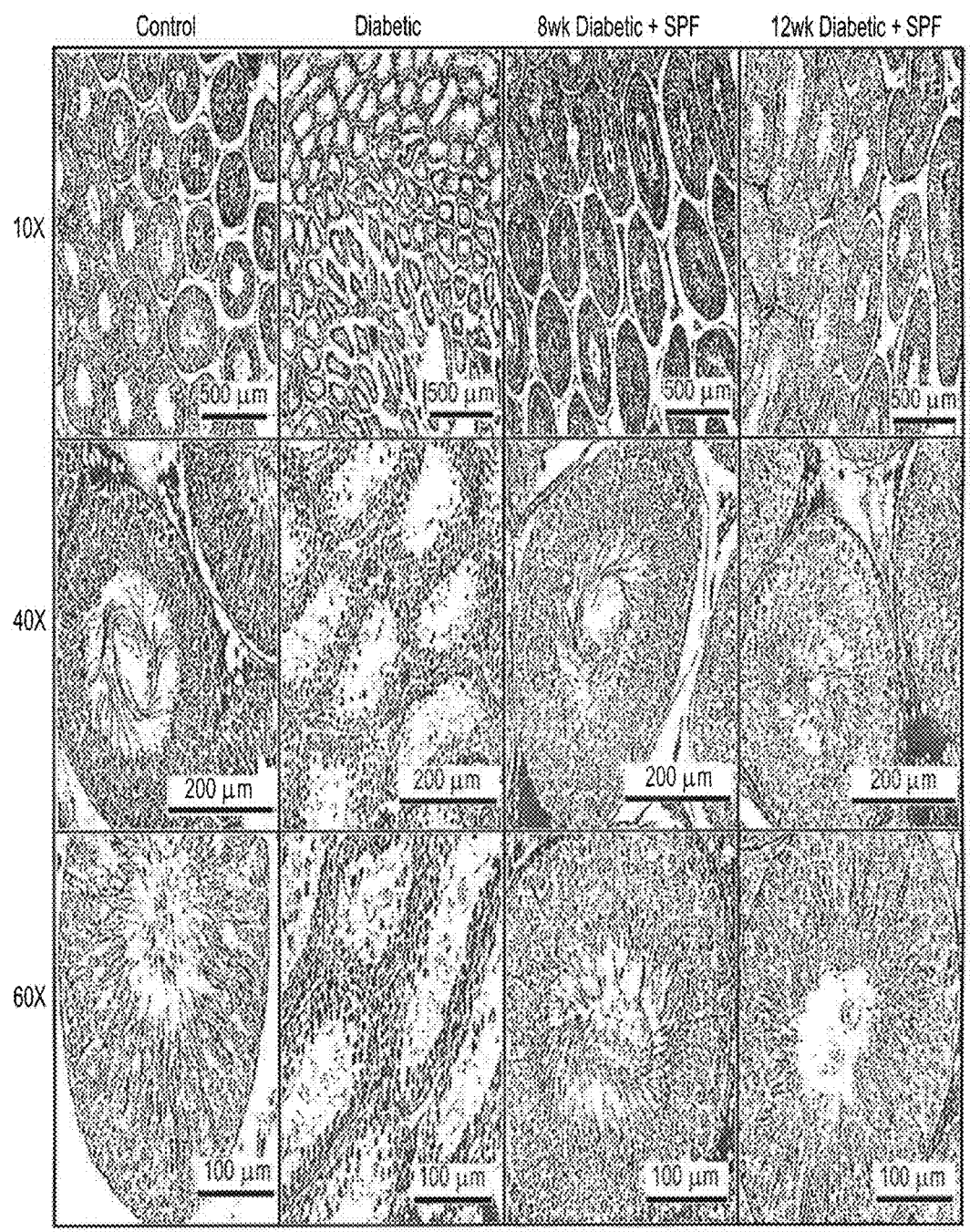
FIG. 3 is a table providing the histological analysis at different magnifications of the seminiferous tubules from all of the experimental groups.

Histological analysis (H & E stain) of the seminiferous tubules of STZ-induced diabetic untreated animals revealed remarkable atrophy and degeneration in the somniferous tubule of the testes of STZ-induced diabetic animals at different magnifications, as shown in the second column of FIG. 3, compared to control animals (1st column). The number of degenerating germ cells was greater in the diabetic untreated group than in the controls. There was evidence of severe shrinkage of the seminiferous tubules and many immature spermatids with abnormal appearance compared to the normal control group. There was no evidence of sloughed Sertoli cells or germ cells in the tubular lumen throughout the testes. Further, Sertoli cell vacuolation, immature germ cell shedding, spermatocyte arrest, and low sperm volume were observed in seminiferous tubules. Vascular dilation and congestion were detected in the interstitial tissue. Immature germ cells were found in epididymal tubule lumina. However, following 8- and 12-weeks treatment with SPF (Fraction-B), the diabetic-treated animals showed amazing recovery in histology of the tubules and cellular morphology similar to normal control animals as shown in the third and fourth columns of FIG. 3. Both 8- and 12-weeks treated animals showed normal spermatogonia, spermatocytes, spermatids and Sertoli cells.

The mean morphologic testicular damage was assessed by the Johnson's scoring system in the four experimental groups. Johnson's score description for seminiferous tubules changes in testes is as follows: "10" indicates complete spermatogenesis and perfect tubules; "9" indicates many spermatozoa present but disorganized spermatogenesis; "8" indicates only a few spermatozoa present; "7" indicates no spermatozoa but many spermatids present; "6" indicates only a few spermatids present; "5" indicates no spermatozoa or spermatids present but many spermatocytes present; "4" indicates only a few spermatocytes present; "3" indicates only spermatogonia present; "2" indicates no germ cells present; and "1" indicates neither germ cells nor Sertoli cells present. In total, 10 tubules were examined per slide and each slide was scored on a scale of 1-10 based on the level of spermatogenesis (Table 1).

TABLE 1

Johnson Score for Assessing Spermatogenesis in Testicular Biopsy

| Groups | Johnsons Score ± S.E. |
| --- | --- |
| Control | 9.5 ± 0.049 |
| Diabetic | 3.5 ± 0.071 |
| 8wk Diabetic + SPF | 8.5 ± 0.191 |
| 12wk Diabetic + SPF | 9.0 ± 0.220 |

Figure 4:
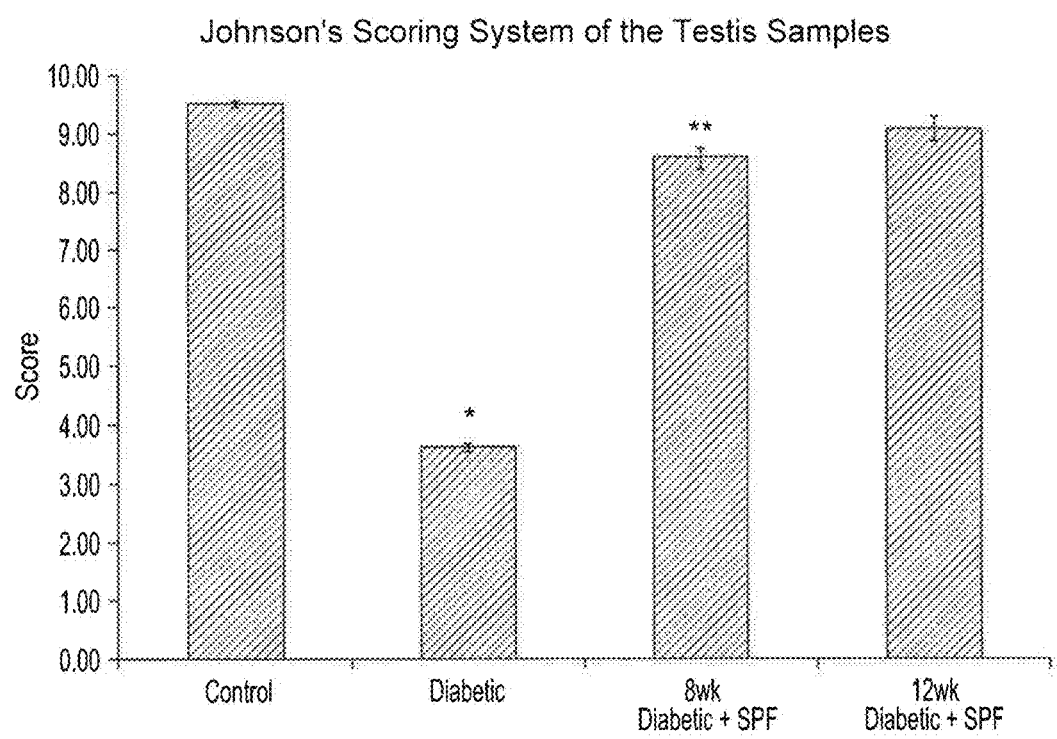
FIG. 4 is a graph showing the mean morphologic testicular damage assessed by the Johnson's scoring system for all of the experimental groups.
Figure 5A:
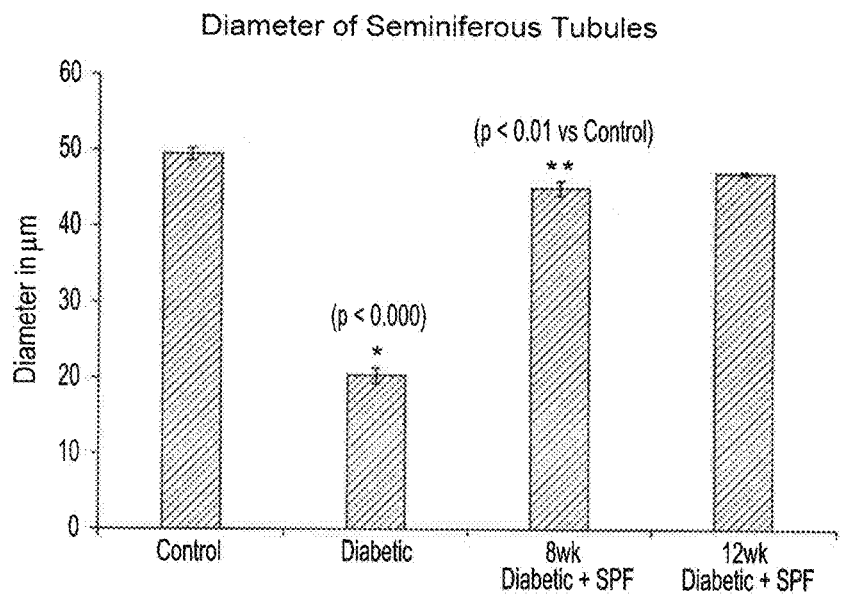
FIG. 5A is a graph showing the diameter of the seminiferous tubules for all of the experimental groups.
Figure 5B:
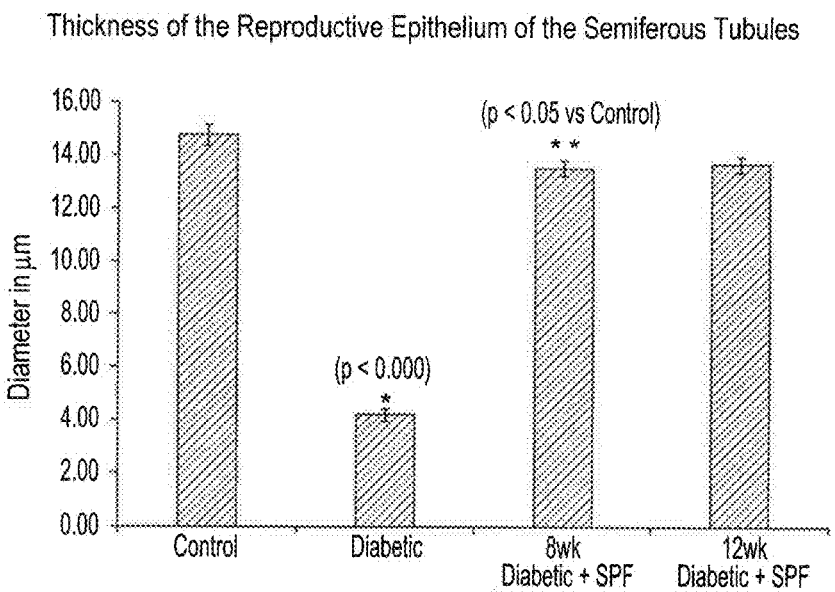
FIG. 5B is a graph showing the thickness of the reproductive epithelium of the seminiferous tubules for all of the experimental groups.

The testes from the diabetic untreated group showed significant low scores (p<0.000) compared to control testes (FIG. 4). The average Johnson's score for the normal Control and Diabetic untreated groups was 9.5+0.049 and 3.5+0.071, respectively. In contrast, the diabetic rats treated with Fraction-B for 8 weeks and 12 weeks exhibited significantly (p<0.000) higher scores (8.5+0.191 and 9.0+0.220) compared to the diabetic untreated group. However, the 8-weeks treated animals showed significantly lower Johnson's score (p<0.002) than the control group. The mean diameter of seminiferous tubules of testes from all the experimental groups is shown in FIG. 5A. The thickness of the reproductive epithelium of the seminiferous tubules of testes from all the experimental groups is shown in FIG. 5B. The STZ-induced diabetic untreated group showed less mean diameter (FIG. 5A) compared to controls (p<0.000). Likewise, the thickness of the reproductive epithelium of the seminiferous tubules (FIG. 5B) was much reduced in the diabetic untreated groups when compared with their controls (p<0.000). The SPF Fraction-B treatment of 8 weeks and 12 weeks diabetic animals increased significantly both the diameters and thickness of the reproductive epithelium of the seminiferous tubules to control values.

Example 4

Sperm Parameters in Diabetic Rats with or without Catfish Fraction-B Treatment

Figure 6A:
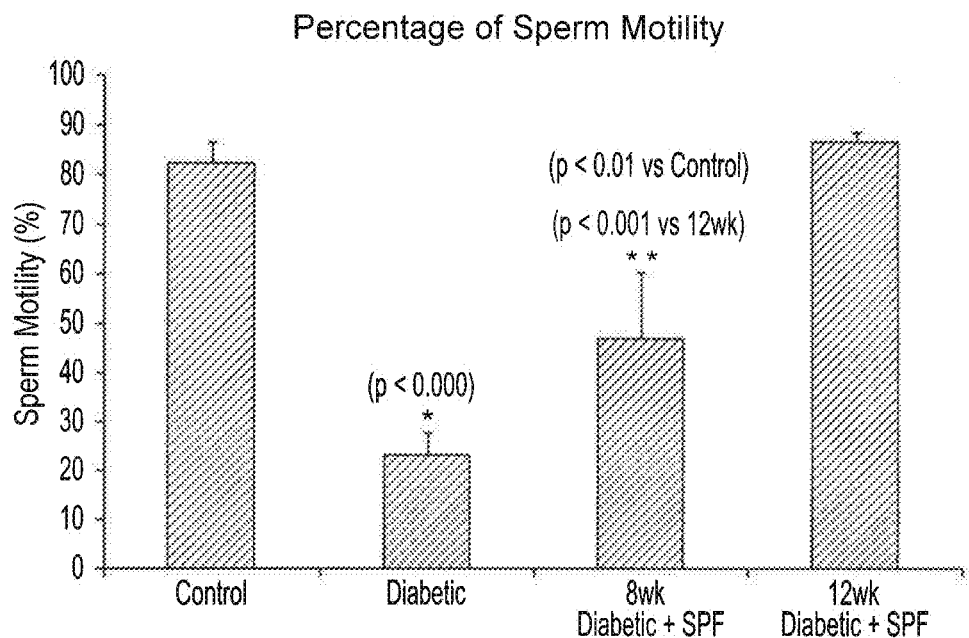
FIG. 6A is a graph showing the percentage of sperm motility for all of the experimental groups.

In diabetic untreated rats, the sperm motility decreased to almost 80% below that of normal control rats (P<0.000; FIG. 6A). However, the SPF Fraction-B treated animals showed a significant recovery of 50% and more than 100% after 8 weeks and 12 weeks, respectively, as compared to untreated diabetic rats. The sperm motility in the 8-weeks Fraction-B treated group still lagged behind the control (P<0.01) and the 12-week diabetic+SPF ((P<0.001) treated groups.

Figure 6B:
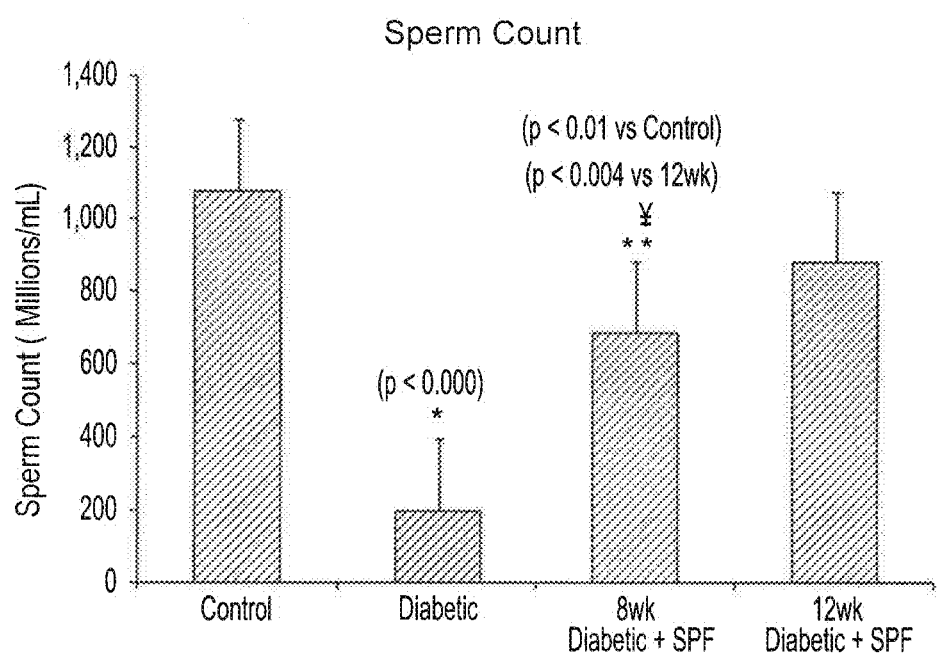
FIG. 6B is a graph showing the sperm count for all of the experimental groups.

Likewise, diabetes decreased the sperm count to more than 80% below normal control values (P<0.001; FIG. 6B). Fraction-B treated rats showed approximately 60% and 85% increase after 8 weeks and 12 weeks of treatment, respectively, compared to diabetic untreated rats (P<0.001; P<0.0001). The sperm count of the 12 weeks catfish Fraction-B treated group showed no significant difference compared to control normal rats.

Example 5

Apoptotic Markers

Figure 7:
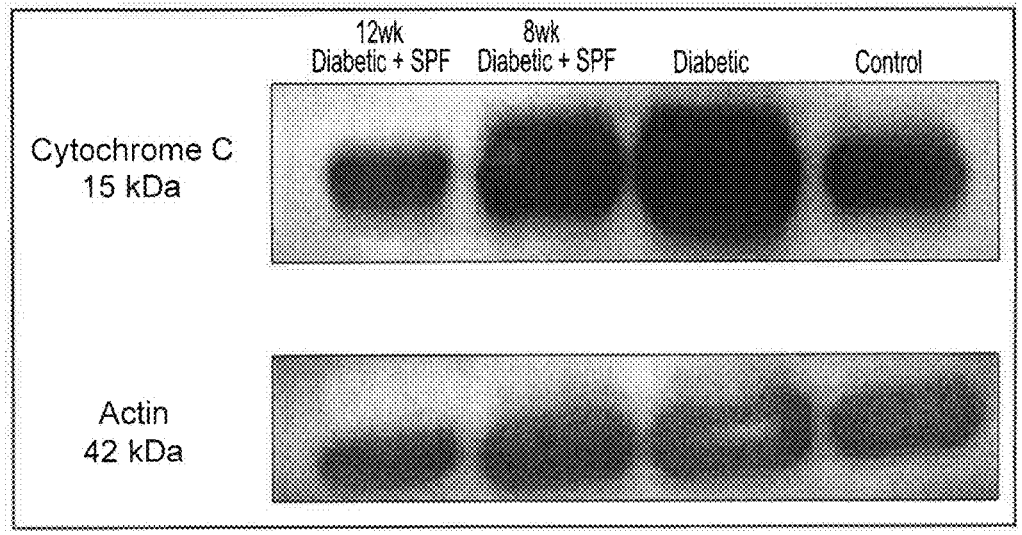
FIG. 7 depicts the Western blot analysis of cytochrome C from the cytoplasmic fractions of the testes for all of the experimental groups.

The release of mitochondrial cytochrome C and the activation of caspase-3 in diabetic animals occur at an early stage of apoptotic cell death. Quantitative analysis of Western blotting showed a significant (P<0.01) increase in the cytochrome C release expression in the diabetic animals compared to the control group (FIG. 7). Post-treatment with Fraction-B significantly (p<0.01) decreased the mitochondrial release of cytochrome C compared to the testes of the diabetic untreated animals. Cytochrome C release showed significant (p<0.001) decrease in 12 week diabetic+SPF group compared to diabetic animals.

Figure 8:
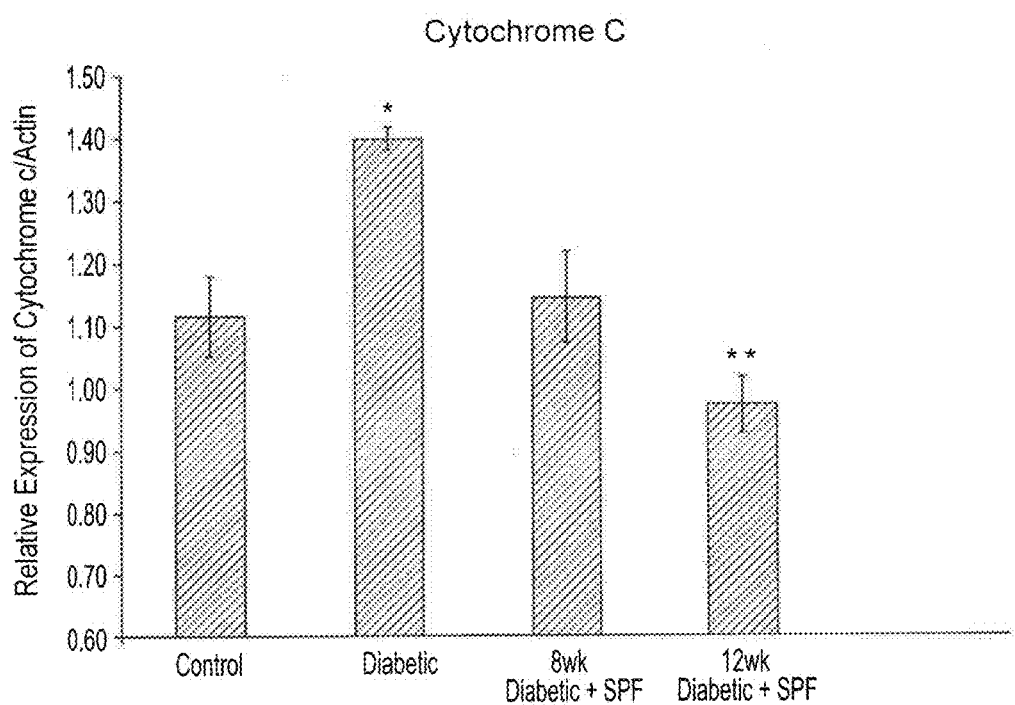
FIG. 8 is a graph showing the level of cytochrome C release for all of the experimental groups.

Western blot analysis also revealed that the level of cleaved (activated) forms of caspase-3 was increased in the diabetic untreated animals (FIG. 8) compared to normal control rats. However, the SPF Fraction-B treatment significantly (*P<0.000) decreased the level of activated caspase-3 in 8 weeks and 12 weeks diabetic groups compared with diabetic untreated animals. Further, the 12 weeks Fraction-B treated rats showed significant (P<0.02) decrease in caspase-3 compared to 8 week diabetic+SPF group.

Figure 9:
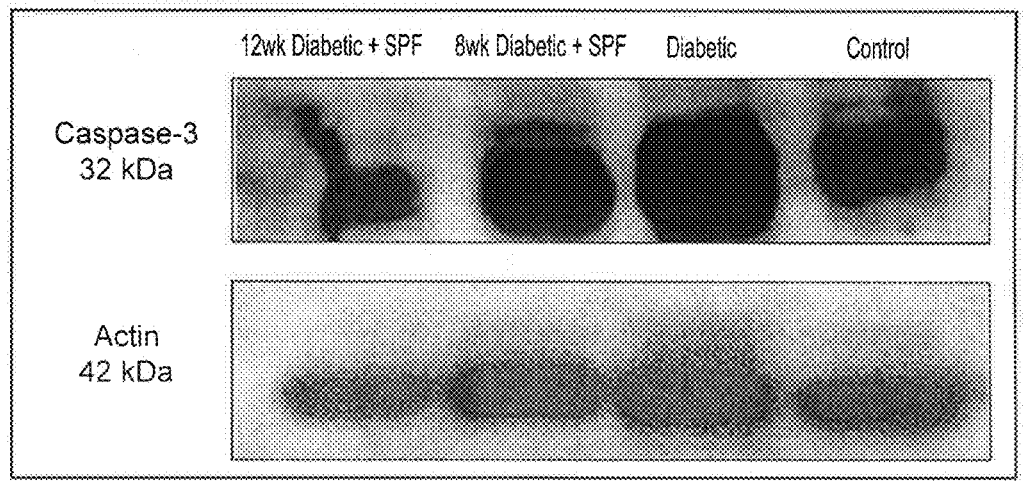
FIG. 9 depicts the Western blot analysis of activated caspase-3 in testes samples.
Figure 10:
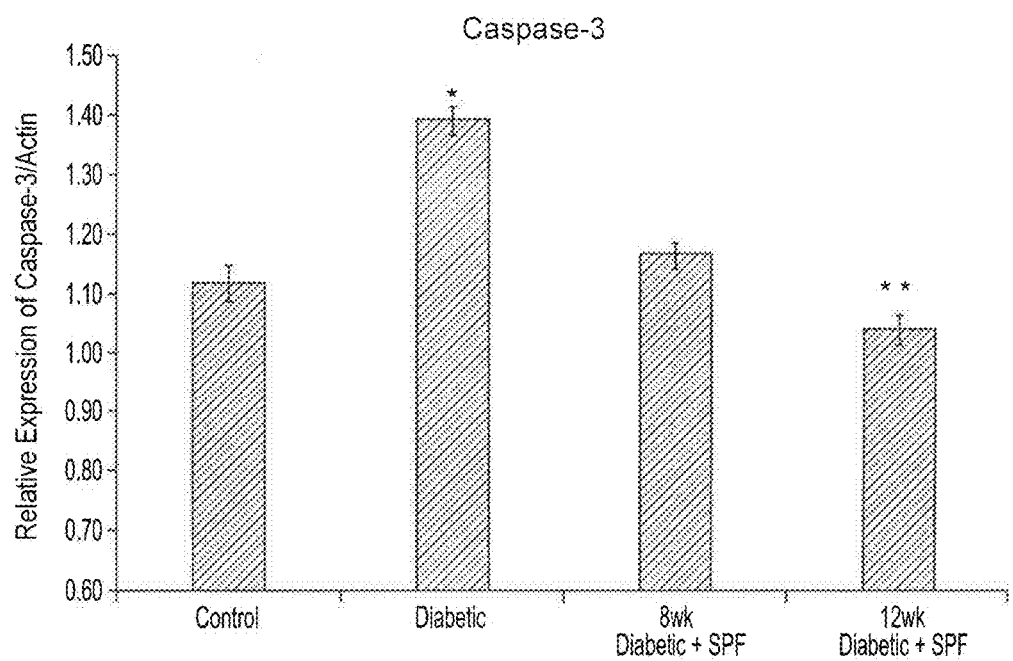
FIG. 10 is a graph showing quantitative analysis of Western blotting showing the level of active caspase-3 in testes samples.
Figure 11:
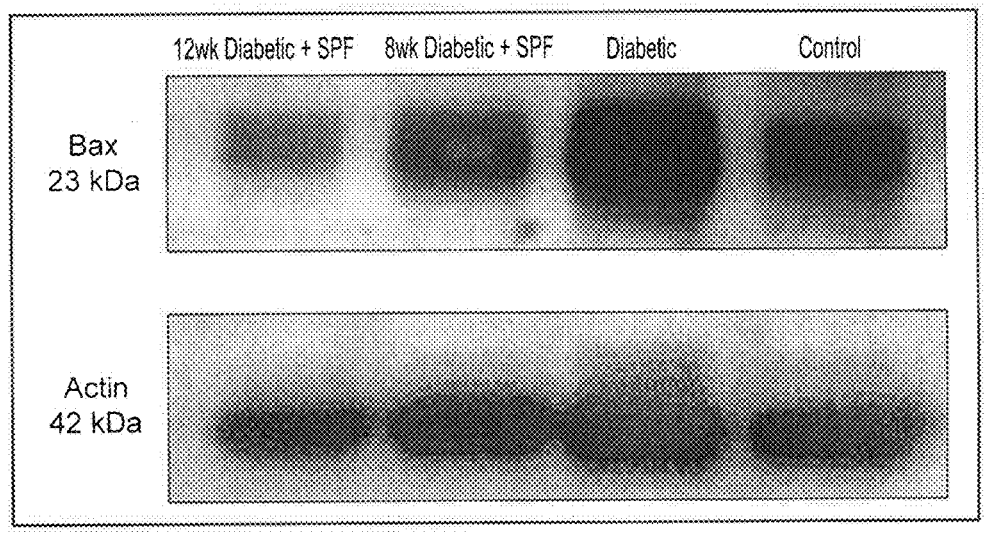
FIG. 11 depicts the Western blot analysis of Bax c from the cytoplasmic fractions of the testes for all of the experimental groups.
Figure 12:
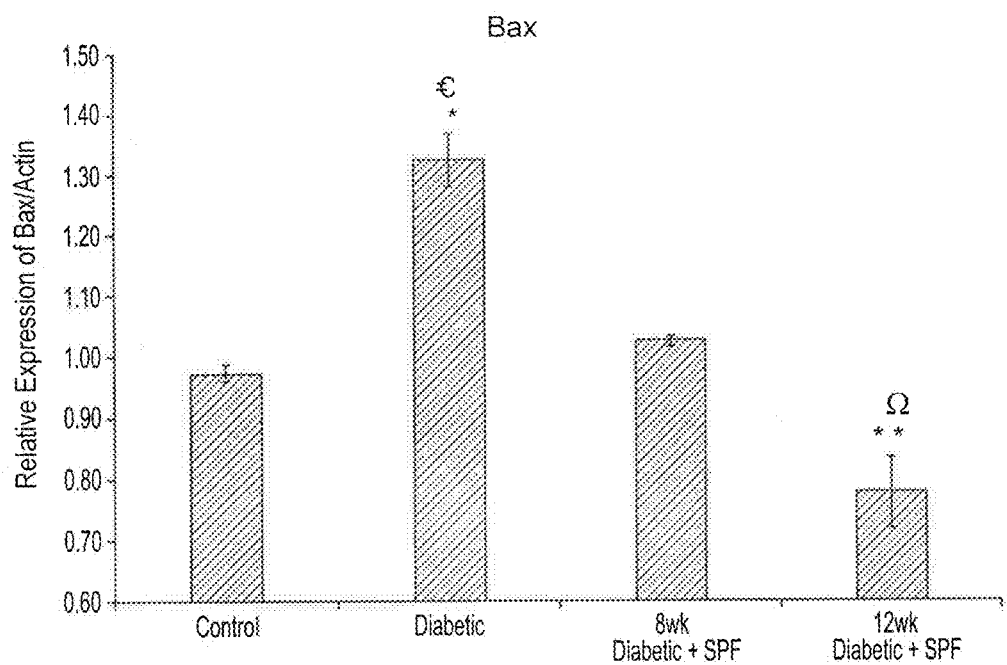
FIG. 12 is a graph showing quantitative analysis of Western blotting showing the level of Bax c expression for all of the experimental groups.

Western blot analysis revealed that Bax protein is also markedly up-regulated in the diabetic group compared to 12 week diabetic+SPF (P<0.000) group and (P<0.001) control and 8 week diabetic+SPF groups (FIGS. 9-10). In contrast, Fraction-B IP administration in STZ-induced diabetic rats significantly reduced the expression levels of Bax compared to expression of Bax in diabetic untreated animals. Further, the 12 week diabetic+SPF group showed a significant decrease in the expression of Bax protein compared to 8 week diabetic+SPF (P<0.001) and control normal (P<0.03) groups.

These results indicated that 8- or 12-weeks SPF (Fraction-B) treatment inhibits cytochrome C release and caspase-3 activation and Bax protein expression in the testes of diabetic animals. In turn, the pro apoptotic pathway is turned off to protect the different cell types (spermatogonia, spermatocytes, spermatids and Sertoli cells) from cellular damage and ultimate death due to the hyperglycemia environment of the diabetic animals.

It is to be understood that the method for treating infertility is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for treating male infertility, comprising:
   (a) providing a therapeutic composition, the therapeutic composition including a soluble protein fraction prepared by fractionating epidermal gel secretions of catfish; and
   (b) administering a therapeutically effective amount of the therapeutic composition to a male patient suffering from infertility.

2. The method for treating infertility according to claim 1, wherein the soluble protein fraction includes 87% soluble proteins and 13% lipids.

3. The method according to claim 1, wherein the fractionating comprises:
   mixing the epidermal gel secretions with an extraction buffer to provide an extract;
   homogenizing the extract with a homogenizer to provide a homogenate; and
   centrifuging the homogenate to provide the soluble protein fraction and an insoluble protein fraction.

4. The method according to claim 3, wherein the extraction buffer comprises phosphate buffered saline.

5. The method according to claim 3, wherein the fractionating further comprises:
   fractionating the insoluble protein fraction to provide an additional soluble protein fraction and an additional insoluble protein fraction; and
   adding the additional soluble protein fraction to the soluble protein fraction obtained by fractionating the epidermal gel secretions.

6. The method according to claim 3, further comprising determining whether the soluble protein fraction includes 87% soluble proteins and 13% lipids.

7. The method according to claim 6, further comprising adding an additional lipid fraction to the soluble protein fraction in an amount sufficient to raise the lipid concentration to 13% of the total aggregated weight of the lipids and proteins in the fraction.

8. The method according to claim 1, wherein the catfish is Arabian Gulf catfish (*Arius bilineatus* (Valenciennes)).

9. The method according to claim 1, wherein the therapeutic composition is administered by subcutaneous injection.

10. The method according to claim 1, wherein the therapeutic composition is administered by intraperitoneal injection.

11. The method according to claim 1, wherein the therapeutic composition is administered orally through sublingual placement of the preparation as tablets.

12. The method according to claim 1, wherein the therapeutically effective amount includes 3 mg to 4 mg of the soluble protein fraction per kilogram of body weight of the patient per day.

13. The method according to claim 1, wherein the therapeutically effective amount includes 3 mg to 3.5 mg of the soluble protein fraction per kilogram of body weight of the patient per day.

14. A method for treating male infertility, comprising:
   (a) providing a therapeutic composition, the therapeutic composition including a soluble protein fraction prepared from epidermal gel secretions of catfish, the soluble protein fraction including 87% soluble proteins and 13% lipids; and
   (b) administering a therapeutically effective amount of the therapeutic composition to a male patient suffering from infertility.

15. The method according to claim 14, wherein the soluble protein fraction is prepared by:
   mixing the epidermal gel secretions with an extraction buffer to provide an extract;
   homogenizing the extract with a homogenizer to provide a homogenate;
   centrifuging the homogenate to provide the soluble protein fraction and an insoluble protein fraction; and
   adjusting the lipid concentration in the soluble protein fraction to achieve a soluble protein fraction having 87% soluble proteins and 13% lipids by weight.

16. The method according to claim 14, wherein the therapeutic composition is administered by interperitoneal injection.

17. The method according to claim 14, wherein the therapeutic composition is administered by subcutaneous injection.

18. The method according to claim 14, wherein the therapeutic composition is administered orally through sublingual placement of the preparation as tablets.

19. The method according to claim 14, wherein the therapeutically effective amount includes 3 mg to 4 mg of the soluble protein fraction per kilogram of body weight of the patient.

20. The method according to claim 14, wherein the therapeutically effective amount includes 3 mg to about 3.5 mg of the soluble protein fraction per kilogram of body weight of the patient.

* * * * *